United States Patent [19]

Varco

[11] Patent Number: 5,047,177

[45] Date of Patent: Sep. 10, 1991

[54] CONDITIONING SHAMPOO COMPOSITIONS CONTAINING CATIONIC GUM DERIVATIVE AND POLYAMINE CONDENSATION PRODUCT AS SOLE CONDITIONING AGENTS

[75] Inventor: Joseph Varco, Fairfield, Conn.

[73] Assignee: Clairol Incorporated, New York, N.Y.

[21] Appl. No.: 516,406

[22] Filed: Apr. 30, 1990

[51] Int. Cl.$^5$ .................. A61K 7/075; C11D 1/65; C11D 3/30; C11D 3/37
[52] U.S. Cl. .................. 252/548; 252/173; 252/174.17; 252/174.21; 252/174.23; 252/544; 252/547; 252/550; 252/551; 252/DIG. 2; 252/DIG. 5; 252/DIG. 13; 424/70
[58] Field of Search .......... 252/DIG. 2, DIG. 13, 252/174.23, 174.17, DIG. 5, 14, 548, 544, 545, 546, 173, 174.21

[56] References Cited

U.S. PATENT DOCUMENTS

| | | | |
|---|---|---|---|
| 3,987,162 | 10/1976 | Scheuermann | 424/70 |
| 4,061,602 | 12/1977 | Okerstar et al. | 252/547 |
| 4,292,212 | 11/1981 | Melby | 252/547 |
| 4,298,494 | 11/1981 | Parslow | 252/174.16 |
| 4,676,978 | 6/1987 | Cseh | 424/70 |
| 4,832,872 | 5/1989 | Scandel | 252/547 |

OTHER PUBLICATIONS

CA107(14):120852d, 1987.
CA106(12):89940j, 1986.
CA102(22):190819u, 1984.
CA102(22):190818t, 1984.
CA97(18):150561a, 1982.
CA102(14):119405a, "Guar hydroxypropyl-trimethylammonium Chloride as a Hair Conditioning Agent", Busch et al., 1984.

*Primary Examiner*—Paul Lieberman
*Assistant Examiner*—A. Beadles-Hay
*Attorney, Agent, or Firm*—Charles J. Zeller

[57] ABSTRACT

A conditioning shampoo composition consisting essentially of an anionic surfactant, a cationic gum derivative, a polyamine condensation product, and water.

10 Claims, No Drawings

CONDITIONING SHAMPOO COMPOSITIONS CONTAINING CATIONIC GUM DERIVATIVE AND POLYAMINE CONDENSATION PRODUCT AS SOLE CONDITIONING AGENTS

FIELD OF THE INVENTION

The present invention relates to shampoo compositions for hair, which impart a conditioning effect to the hair. Accordingly, the shampoo compositions of the present invention can be used without the need to apply a conditioner to the hair after the shampooing process has been completed. More specifically, the compositions of the present invention contain, in addition to an anionic surface active agent, a cationic guar derivative and an ethoxylated polyamine, which act in concert to provide the desired conditioning effect.

BACKGROUND OF THE INVENTION

Typically, hair is cleaned by first shampooing the hair with a composition containing an anionic surface active agent, rinsing the hair with water to remove the shampoo, and thereafter treating the hair with a conditioning composition containing a cationic surfactant as the conditioning active. Many consumers, however, find this multistep procedure cumbersome. Additionally, it is more expensive than a single-step process because two products—the shampoo and the conditioner—must be purchased.

Products containing both the shampoo and the conditioner in one composition are known, as indicated below. However, one of the problems in providing such products is the known incompatibility between the anionic surfactant needed for shampooing and the cationic surfactant needed for conditioning.

As noted above, notwithstanding the difficulties in obtaining composite shampoo-conditioning products, such products are known. Thus, U.S. Pat. No. 4,788,066 to Bolich, Jr. et al discloses a conditioning shampoo comprising 5-50% anionic surfactant, 0.1-10% insoluble, nonvolatile silicone, 0.4-5% xanthan gum, and water.

U.S. Pat. No. 4,061,602 to Oberstar et al discloses a conditioning shampoo composition containing a cationic derivative of a polygalactomannan gum, the quaternary ammonium segment of the gum having the structure:

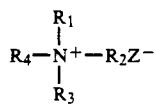

wherein $R_1$, $R_2$ and $R_3$ are selected from among alkyl, aryl and substituted aryl groups, $R_4$ is selected from between epoxyalkyl and halohydrin groups, and $Z^-$ is an anion such as $Cl^-$, $Br^-$, $I^-$ and $HSO_4^-$. The Oberstar et al compositions also include anionic detergents, amphoteric detergents, nonionic detergents, pH adjustment agents such as citric acid, and other conventional adjuvants. The preferred gum is 3-(trimethylamino)-2-hydroxypropyl guar chloride.

It is also known to incorporate ethoxylated polyamines in a conditioning shampoo. Thus, Henkel's Technical Data for Polyquart H, an ethoxylated polyamine, discloses a herbal conditioning shampoo containing 35% Standapol ES-2 (sodium laureth sulfate); Standamid LD (lauramide DEA); 3% Polyquart H (a 50% aqueous solution of PEG 15 Tallow Polyamine); 3% Hexaplant Richter (plant extracts); 1% sodium chloride; 66% water, and the remainder perfumes, dyes and preservatives. Henkel also discloses a similar composition comprising 15% Standapol ES-2; 15% Standapol WAQ Spec.; 1.5% Standamid LD; 3% Polyquart H; 1% sodium chloride, 1% ethylene glycol monostearate, and the remainder water.

U.S. Pat. No. 3,987,162 to Scheuermann discloses shampoo compositions of the type set forth in the previous paragraph, which contain 0.1-10% of a water-soluble, hardenable polycondensation products produced by reacting a polyamine having 2 to 10 carbons with an ether of polyoxyalkylene glycol having terminal halogen or hydroxyl and having 2-4 carbons in the alkylene units thereof. These polyamines have more than one hydrogen atom attached to a nitrogen atom and are further reacted with a bifunctional aliphatic compound having epoxide or halohydroxyalkyl functional groups. Polyquart H is within this class of compounds. The compositions of Scheuermann further comprise anionic surfactants, amphoteric surfactants, emulsifying agents thickeners and organic solvents.

U.S. Pat. No 4,676,978 to Cseh discloses aqueous shampoo compositions comprising, in addition to the anionic surfactants recited at column 5, lines 16-44, a mixture of four essential conditioning agents: (1) 0.1-4% 3-(trimethylamino)-2-hydroxypropyl guar chloride; (2) 0.5-5% of a readily water-soluble, hardenable polycondensation product formed by reacting a water-soluble polyamine containing reactive amino groups and having 4 to 6 carbon atoms with an ether of poly $C_2$-$C_3$ alkylene glycol having terminal halohydrin or hydroxyl groups followed by reaction with either epichlorohydrin or the addition reaction product of said polyamine and said ether; (3) 1-4% of an esterification product formed by reacting 1 to 2 moles of $C_8$-$C_{18}$ fatty acid with the adduct obtained by reacting 4 to 20 moles of ethylene oxide with 1 mole of glycerol, and (4) 0.1 to 1% of a polyvinyl pyrrolidone having an average molecular alight of 10,000 to 70,000, all percents being by weight of the compositions. The weight ratio of Cseh's essential conditioning agents (1):(2):(3):(4) is 1:0.5-4:0-.5-4:0.15-0.5 and the weight ratio of the anionic detergent to the mixture of essential conditioning agents is 10:1 to 1:1.

Cseh's data in Table 2 clearly indicates that all four of the essential conditioning agents are necessary to obtain a conditioning effect.

The composition of Cseh is quite complex and requires a high degree of precision in its manufacture to obtain the requisite proportions of ingredients. Accordingly, the composition is expensive to manufacture, which cost is, of course, passed along to the consumer.

It has been found, notwithstanding the disclosure of Cseh, that shampoo compositions containing 3-(trimethylamino)-2-hydroxypropyl guar chloride and the water-soluble polyamine condensation product as the sole conditioning agents provide an excellent conditioning benefit to hair. Moreover, the conditioning benefit of the composition of the present invention is surprisingly better than the effect obtained with either conditioning active incorporated separately. Accordingly, the compositions of the present invention are simpler and less expensive to manufacture than the compositions of Cseh.

SUMMARY OF THE INVENTION

The conditioning shampoos of the present invention consist essentially of by weight of the total composition (a) from about 1 to about 50% of an anionic surfactant; (b) from about 0.1 to about 3% 3-(trimethyl amino)-2-hydroxypropyl guar chloride; (c) from about 0.5 to about 3% of an ethoxylated polyamine having a fatty alkyl residue, and (d) water as the remainder.

DETAILED DESCRIPTION OF THE INVENTION

The conditioning shampoos of the present invention are suitable to simultaneously clean hair and provide hair with a conditioning effect. Hair treated with these compositions is substantially free of tangles, easily combed, and has a low degree of static charge.

The essential active components of the aqueous shampoo compositions of the present invention are an anionic surfactant, a cationic guar derivative, and an ethoxylated polyamine, as described below, the guar derivative and the polyamine constituents being essentially the sole hair conditioning actives present in the composition. By "essentially the sole hair conditioning actives" is meant that other agents contained in the composition and at their concentrations in the composition provide, at best, a minimal effect on the degree of conditioning obtained on hair. In other words, the conditioning effect obtained by shampooing with compositions of the present invention stems substantially from the two essential conditioning agents.

The Anionic Surfactant

Suitable anionic surfactants are those generally incorporated into a shampoo product. Generally, the anionic surfactant is a water-soluble alkyl or alkyl aryl sulfate or sulfonate having from about 8 to about 22 carbons, preferably from about 12 to about 18 carbons, in the alkyl radical, which may be straight or branched chain, and also includes such classes of compounds ethoxylated with from 1 to 5 mols, preferably 1 to 3 mols, ethylene oxide per molecule. The sulfate or sulfonate group is typically base-neutralized to provide an alkali metal, especially sodium or potassium, ammonium, or mono-, di- or trialkanolium cation.

Illustrative anionic surfactants of the above-named classes include:
Sodium cetyl sulfate
Sodium myristyl sulfate
Sodium lauryl sulfate
Sodium tallow sulfate
Sodium decyl sulfate
Sodium decylbenzene sulfonate
Sodium tridecylbenzene sulfonate
Sodium $C_{14}$-$C_{16}$ olefin sulfonate
Sodium $C_{12}$-$C_5$ alcohol sulfate
Sodium lauryl ether sulfate
Sodium myristyl ether sulfate
Sodium polyoxyethylene (5 mols EO) lauryl ether sulfate
Sodium polyoxyethylene (12 mols EO) lauryl ether sulfate
Sodium nonylphenyl ether sulfate
Sodium polyoxyethylene (1 to 4 mols EO) $C_{12}$-$C_{15}$ alkyl ether sulfate
Sodium lauryl sulfoacetate Although sodium salts are identified in the table above, the other cations previously named would also be suitable, especially ammonium.

Other suitable anionic surfactants include sulfosuccinates, e.g., sodium dioctyl sulfosuccinate, disodium lauryl sulfosuccinate and the disodium polyoxyethylene (1 to 4 mols EO) lauryl alcohol half ester of sulfosuccinic acid; sulfated monoglycerides, e.g., sodium cocomonoglyceride sulfate; sarcosinates, e.g., sodium cocoyl sarcosinate and sodium lauroyl sarcosinate; esters of isethionic acid, e.g., sodium cocoyl isethionate and sodium lauroyl isethionate; taurides, e.g., sodium N-methyl-N-cocoyl taurate and sodium N-methyl-N-oleoyl taurate. Soaps may also be incorporated, e.g., sodium stearate, sodium laurate and sodium isethionate. Also suitable are protalbinic and lysalbinic acid derivatives, generally classed as Maypon surfactants.

The anionic surfactants may be used singly or in combination. Often, two or more anionic surfactants may be blended to achieve a desired visosity, cleaning benefit, or other property.

The anionic surfactants typically comprise from about 1 to about 50% by weight of the composition. However, the concentration is not deemed critical so long as the concentration employed does not interfere in the physical stability of the product shampoo. Preferably, the anionic surfactants are present in an amount of from about 5 to about 35%, most preferably from about 10 to about 25%, by weight of the composition.

Preferred anionic surfactants are sodium or ammonium $C_{12}$ to $C_{14}$ alkyl sulfates, and sodium or ammonium $C_{12}$ to $C_{14}$ alkyl ether sulfates having 1 to 3 mols ethylene oxide. An especially preferred anionic surfactant system comprises from about 4 to about 15% sodium lauryl sulfate and from about 3 to about 10% sodium lauryl ether sulfate, by weight of the composition.

The Cationic Gum Derivative

The second essential component is a cationic derivative of guar gum or locust bean gum. Such gums are polygalactomannans containing two mannose units with a glycoside linkage and a galactose unit attached to one of the hydroxyl groups of the mannose units. The hydroxyl groups are reacted with certain reactive quaternary ammonium compounds to obtain the cationic derivative.

The quaternary ammonium compounds suitable for preparing the cationic gum derivatives of the present invention have the structure

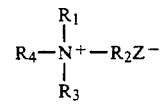

wherein $R_1$, $R_2$ and $R_3$ are alkyl, aryl and substituted alkyl and aryl groups, $R_4$ is selected from the group consisting of epoxyalkyl and halohydrin, and $Z^-$ is an anion, e.g., $Cl^-$, $Br^-$, $I^-$ and $HSO_4^-$. Suitable epoxyalkyl groups have the structure

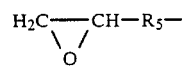

suitable halohydrins have the structure

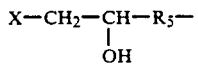

wherein $R_5$ is a divalent alkylene of 1 to 3 carbons and X is a halogen.

Particularly preferred is the compound 3-(trimethylamino)-2-hydroxypropyl guar chloride which has the structure

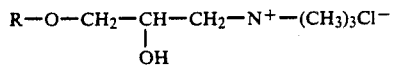

wherein R is the polygalactomannan molecule based on guar, and is sold as Cosmedia Guar 261N by Henkel Corporation.

The cationic gum derivative is present in an amount of from about 0.1 to about 3%, preferably from about 1 to about 2%, by weight of the composition.

The Polyamine Component

The third essential ingredient is a water-soluble, hardenable polyamine. The preparation of the polyamines suitable for use herein is described in U.S. Pat. No. 3,987,162 to Scheuermann and U.S. Pat. No. 4,676,978 to Cseh, both of which are incorporated herein by reference.

Generally, the procedure for preparation of the polyamine described in these references is to react polyamines, especially polyalkylene polyamines, with mono- and/or polyfunctional ether derivatives of polyalkylene oxides, especially polyethylene oxide, but also propylene oxide. The reactive groups contained on the polyethylene oxides are chlorohydrin, glycidyl, hydroxyl, halogen or other radicals capable of anion formation. The resultant reaction product is reacted with (i) epoxides having more than one epoxide group, (ii) a halohydrin group such as epichlorohydrin, (iii) a bifunctional reaction product obtained by reaction of (i) or (ii) with a glycol, diglycol, polyalkylene glycol, glycerin and the like, or (iv) the addition product of the polyamine and the ether.

Suitable polyamines for the synthesis include dipropylene triamine, diethylenetriamine or triethylenetriamine. Suitable polyethylene oxides are those having 10 to 20 moles ethylene oxide. The water-soluble, hardenable polyamine is further reacted to provide terminal aliphatic residues.

Using the CTFA Cosmetic Ingredient Dictionary nomenclature, suitable polyamines are the PEG-n aliphatic polyamines, wherein n is the degree of ethoxylation associated with each ethoxy group. Suitable aliphatic groups are coconut and tallow, as well as other fatty aliphatic residues. Structurally, the CTFA represents this material as

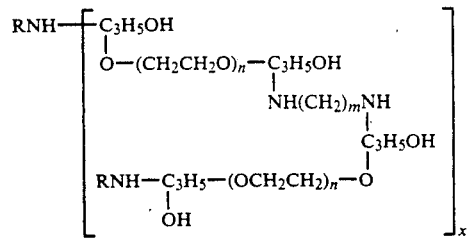

wherein R is oleyl, stearyl, cocoyl or tallow, n has an average value of from about 10 to 20; m has a value of from 2 to 6 and x has a value of from 2 to 4. The tallow-based compound is available as Polyquart H from Henkel Corporation and is sold as a 50% active aqueous solution.

The polyamine actives are present in an amount of from about 0.5 to about 3%, preferably from about 1 to about 2% by weight of the compositions.

Optional Constituents

The compositions of the present invention may also contain optional ingredients which improve the elegance of the product, as set forth below. These optional components are present at a level effective to provide their intended function.

Foam builders or foam stabilizers are materials which increase the quality, volume and stability of the lather. They also enhance viscosity. The preferred foam builders are the fatty acid alkanolamides such as lauroyl diethanolamide, lauroyl monoethanolamide and coconut monoethanolamide. Other foam builders are "super" amides, e.g., Super amide B-5, fatty alcohols, sarcosinates, phosphates and dodecylbenzene sulfonates. The foam builders are typically present in an amount of from about 0.1 to 10%, preferably from about 0.5 to about 5%, by weight of the composition.

Opacifying agents are used in cream and lotion compositions. Suitable opacifying agents are the higher alcohols, such as stearyl and cetyl alcohol, and the higher acids such as behenic acid. The glycol mono- and distearates are also effective opacifiers. Sodium chloride and sodium sulfate can also be used as opacifying aids, when used in concentrations that do not cause gelation. Alkaline earth metal fatty acid soaps, such as calcium stearate and magnesium stearate, are also suitable. Magnesium silicates are also useful for this purpose. Opacifying agents are typically present in an amount of from 0.1 to about 10%, preferably from about 0.5 to about 5%, by weight of the composition.

Viscosity-control agents are often useful to stably regulate the viscosity of the ingredients of the shampoo composition. Suitable viscosity-control agents are lower alcohols, e.g., isopropyl and butyl alcohol, lower glycols, e.g., propylene glycol and diethylene glycol, terpineol and diethyl carbitol. These agents are typically present in an amount of from about 0.1 to about 5%, preferably from about 0.5 to 2.5% by weight of the composition.

Sequestering agents are useful to prevent the formation of a lime soap film when shampooed hair is rinsed with hard water. Suitable materials are ethylenediaminebetraacetic acid (EDTA), citric acid, sodium xylene sulfonate and sodium naphthalene sulfonate. Sequestering agents are typically present in an amount of from about 0.1 to about 5%, preferably from about 0.1 to about 1%, by weight of the composition.

Although incorporation of nonionic surfactants is not preferred because of their low foaming capability, they are suitable for use in concert with the anionic surfactants identified above. The nonionic surfactants are useful in the compositions of the present invention, however, because they offer excellent resistance to hard water.

The suitable nonionics are characterized by long chain oxyethylene or oxyethylene-oxypropylene units. Illustrative materials are the polyoxyethylene octyl and nonyl phenyl ethers having above about 6 mols ethylene oxide, preferably about 6 to 15 mols ethylene oxide, e.g., the Igepal surfactants; block copolymers of ethylene and propylene oxide generally designated as Pluronic surfactants, and polyoxyethylene sorbitan monolaurates and monostearates, generally designated as Tween surfactants. However, these classes of nonionic surfactants should not be regarded as limiting.

The nonionic surfactant is generally present in an amount of from 0.1 to about 10%, preferably from about 0.1 to about 5%, by weight of the composition.

Amphoteric surfactants have a cationic characteristic in acid pH compositions. Accordingly, they would not be preferred in compositions of the present invention that have an acid pH, in view of the known incompatibility of anionic and cationic surfactants. They may have some usefulness, however, in basic pH compositions of the present invention. Illustrative amphoterics are N-alkyl-β-imino dipropionates and the basic ammonium compounds derived from 2-alkyl-substituted imidazoline, e.g., Miranol surfactants.

Thickening agents increase the viscosity of the shampoo product. Suitable materials are natural gums such as tragacenth, xanthan, acacia and locust bean, and synthetic gums such as hydroxypropylcellulose and methyl cellulose. Polyvinyl alcohols can also be used. Alkyolamides, "super" amides and the glycol or glycerol stearates may also be used. The thickening agents are present in an amount to provide the desired viscosity, typically from about 0.1 to about 10%, preferably from about 0.1 to about 5%, by weight of the composition.

Preservatives are typically present to prevent degradation from bacterial and mold action. Formaldehyde, methyl and propylhydroxybenzoates, dimethylol dimethyl hydantoins and 2-phenoxyethanol are preferred. They are present in an amount of from about 0.01 to about 1% by weight of the composition.

Other additives include antioxidants such as sodium sulfite, suspending agents, sunscreens, and pH control agents such as citric acid, each of which is present in an amount, usually less than 5% by weight of the composition, effective to provide its intended function. An antidandruff component may also be included at an effective level, e.g., selenium sulfide.

The pH of the shampoo compositions of the present invention may be between 4 to about 10. Preferably, the pH is about the same as that of skin—i.e., from about 5 to about 7. The viscosity of the composition is typically from about 500 to about 10,000 cps, preferably from about 500 to about 5,000 cps.

The present invention is further illustrated by the examples below, which are not intended to be limiting.

EXAMPLE 1

A conditioning shampoo composition in accordance with the present invention was prepared by admixing the constituents below.

| Component | A Wt. %* |
| --- | --- |
| Sodium lauryl sulfate | 8.1 |
| Sodium lauryl ether sulfate | 6.75 |
| Cosmedia Guar 261N | 0.46 |
| Polyquart H | 1.50 |
| Coconut monoalkanolamide | 1.0 |
| Cetearyl alcohol | 1.0 |
| Ceteareth 20 | |
| Ethylene glycol distearate | 0.7 |
| Citric acid | 0.3 |
| Antioxidant | 0.25 |
| Preservative | 0.4 |
| Fragrance | 0.9 |
| Water Q.S. | 100% |

*Weight percent based on active ingredient concentration.

EXAMPLES 2-4

Three further compositions were prepared. Composition B was the same as Composition A of Example 1, except it did not contain conditioning constituents, namely, Cosmedia Guar 261N and Polyquart H. Composition C contained 0.46% Cosmedia Guar 261N and 0% Polyquart H; Composition D contained 0% Cosmedia 261N and 1.5% Polyquart H.

The Compositions A-D were tested by shampooing swatches of bleach-damaged hair. The swatches were blindly rated as to wet-combing by a panel of seven judges having experience in assessing the wet-combing work. Each of the judges assigned a value of from 1 to 4 to each swatch, 1 being the easiest to comb and 4 being the most difficult to comb. The results of the average rating is indicated below.

| Composition | Average Rating |
| --- | --- |
| A | 1.14 |
| B | 4.0 |
| C | 2.57 |
| D | 2.28 |

It is seen that the Composition A containing both conditioning agents was markedly superior in wet-combing benefit as compared to the Compositions B through D.

What is claimed is:

1. A conditioning shampoo composition consisting essentially of by weight of the composition (a) from about 1 to about 50% of an anionic surfactant; (b) from about 0.1 to about 3% of a cationic derivative of a polygalactomannan gum, (c) from about 0.5 to about 3% of a readily water-soluble polycondensation product obtained by reacting a water-soluble polyamine containing reactive amino groups and having 4 to 6 carbons with an ether of a poly $C_2$-$C_3$ alkylene glycol having terminal halohydrin or hydroxyl groups followed by reaction with (i) a halohydrin, (ii) an epoxide having more than one epoxide group, (iii) a bifunctional reaction product obtained by reaction of (i) or (ii) with a reactant selected from glycols, diglycols, polyalkylene glycol and glycerin, and (iv) the addition product of said amine and said ether, said component (c) having terminal fatty aliphatic residues, and (d) from 44 to 98.8% water, the components (b) and (c) being essentially the sole hair conditioning components present in the composition.

2. The composition of claim 1 wherein the reactive polyamine is selected from the group consisting of diethylenetriamine, triethylenetriamine and dipropylenetriamine, the alkylene glycol is ethylene glycol, and the aliphatic residue is selected from coconut and tallow radicals.

3. The composition of claim 1 wherein the reactive polyamine is selected from the group consisting of diethylenetriamine, triethylenetriamine and dipropylenetriamine, the alkylene glycol is ethylene glycol, and the aliphatic residue is selected from coconut and tallow radicals, said condensation product being obtained with component (iv).

4. A conditioning shampoo composition consisting essentially of by weight of the composition (a) from about 1 to 50% of an anionic surfactant; (b) from about 0.1 to about 3% of a cationic derivative of a polygalactomannan gum; (c) from about 0.5 to about 3% of a readily water-soluble polycondensation product characterized by the structure

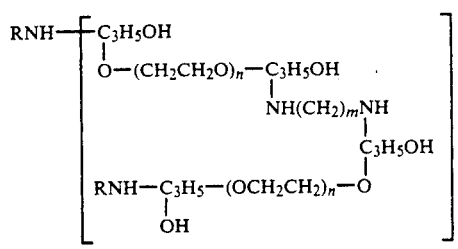

wherein R is a fatty aliphatic residue; n has an average value of from 10 to 20; m has a value of from 2 to 6, and x has an average value of from 2 to 4, and from about 44 to about 98.8% water, the components (b) and (c) being essentially the sole hair conditioning agents present in the composition.

5. The composition of claim 1, 2, 3 or 4 wherein the component (b) is 3-(trimethylamino)-2-hydroxypropyl guar chloride.

6. The composition of claim 5 wherein the component (b) is present in an amount of from about 1 to about 2%.

7. The composition of claim 6 wherein the component (c) is present in an amount of from about 1 to about 2%.

8. The composition of claim 5 wherein the anionic surfactant is present in an amount of from about 10 to about 25%.

9. The composition of claim 8 wherein the anionic surfactant comprises a mixture of about 4 to about 15% sodium lauryl sulfate and from about 3 to about 10% sodium lauryl ether sulfate, said concentrations being by weight of the total composition.

10. The composition of claim 1 or 2 further comprising one or more of: foam builders, opacifying agents, viscosity control agents, sequestering agents, nonionic or amphoteric surfactants, thickening agents and pH control agents, said components being present in an amount effective to provide their intended function.

* * * * *